United States Patent [19]

Nagata et al.

[11] Patent Number: 4,978,792

[45] Date of Patent: Dec. 18, 1990

[54] PROCESS FOR PRODUCING AMINOBENZYLAMINE

[75] Inventors: Teruyuki Nagata; Akihiro Tamaki; Katsuzi Watanabe, all of Fukuoka; Akihiro Yamaguchi, Kanagawa, all of Japan

[73] Assignee: Mitsui Toatsu Chemicals, Inc., Tokyo, Japan

[21] Appl. No.: 323,087

[22] Filed: Mar. 14, 1989

Related U.S. Application Data

[63] Continuation of Ser. No. 241,968, Sep. 8, 1988, abandoned, which is a continuation-in-part of Ser. No. 129,916, Dec. 3, 1987, abandoned, which is a continuation of Ser. No. 668,705, Nov. 6, 1984, abandoned.

[51] Int. Cl.$^5$ ............................................ C07C 211/00
[52] U.S. Cl. ..................................... 564/384; 564/385
[58] Field of Search ................................. 564/384, 385

[56] References Cited

PUBLICATIONS

J. R. Griffith et al., *NRL Report* 6439, *J. Medicinal Chem.*, vol. 20, No. 9, (1977), Neil C. Brown et al.
*Synthetic Communications* 7, 71–78 (1977), "A Convenient Synthesis of Amines", A. Siddiqui et al.
*J. Am. Chem. Co.*, vol. 71, 2137 (1949), "The Selective Replacement of the Aromatic Primary Amino Group by Hydrogen in Aromatic-Aliphatic Diamines", N. Kornblum.

*Primary Examiner*—Robert V. Hines
*Attorney, Agent, or Firm*—Jeffers, Hoffman & Niewyk

[57] ABSTRACT

A commercially advantageous process for producing m- or p-aminobenzylamine is provided, which is characterized by subjecting m- or p-nitrobenzaldehyde and ammonia to catalytic reduction in the presence of a reducing catalyst in an organic solvent; in the reduction, when nitrobenzaldehyde and ammonia are in advance made a mixed solution in an organic solvent, and this solution is added in divided manner, the yield being further improved.

2 Claims, No Drawings

PROCESS FOR PRODUCING AMINOBENZYLAMINE

CROSS-REFERENCE TO RELATED APPLICATIONS

This is a continuation of application Ser. No. 241,968, filed Sept. 8, 1988, which is a continuation-in-part of application Ser. No. 129,916, filed Dec. 3, 1987, now abandoned, which is a continuation of application Ser. No. 668,705 filed Nov. 6, 1984, now abandoned.

BACKGROUND OF THE INVENTION

1. Field of the Invention

This invention relates to a novel process for producing m-or p-aminobenzylamine, and more particularly it relates to a commercially advantageous process for producing the same.

Aminobenzylamine is an important material used as a curing agent for epoxy resins, a raw material for polyamides and polyimide and a raw material for intermediates for pesticides and pharmaceuticals.

2. Description of the Prior Art

As for aminobenzylamine, there have so far been known processes for producing it using nitrobenzaldehyde or nitrobenzonitrile as starting raw material. For example, as for the process using the former as starting raw material, the following ones have been known:

(i) A process wherein from m-nitrobenzaldehyde is derived nitrobenzylbromide, which is then reacted with potassium phthalimide to obtain N-(m-nitrobenzyl)-phthalimide which is then subjected to a two-stage reduction to obtain m-aminobenzylamine (yield: Ca. 20%) (N. Kornblum et al., J.Am. Chem. Co., 71, 2137(1949)).

(ii) A process wherein m-nitrobenzaldehyde is reacted with phenylhydrazine to obtain a hydrazone compound which is then subjected to catalytic reduction to obtain m-aminobenzylamine (yield: 60%) (A. Siddiqui et al, Synth Commn, 7, 71–78 (1977)).

(iii) From m-nitrobenzaldehyde is obtained m-nitrobenzaldoxime which is then subjected to high pressure catalytic reduction with Raney nickel catalyst to obtain m-aminobenzylamine (yield: 52%) (J.R. Griffith et al, NRL Report 6439)).

On the other hand, as for the process using the latter as starting raw material, the following ones have been known:

(iv) A process wherein p-aminobenzonitrile derived from p-nitrobenzonitrile is reduced with lithium aluminum hydride to obtain p-aminobenzylamine (yield: 37%) (N.C. Brown et al, J. Medicinal Chem., 20, 1189 (1977)).

(v) A process wherein M-nitrobenzonitrile is subjected to high pressure catalytic reduction with Raney nickel catalyst to obtain m-aminobenzylamine (yield: 49%) (J.R. Griffith et al., NRL Report 6439)).

However, according to the above processes (i) and (ii), a relatively expensive compound such as potassium phthalimide or phenylhydrazine is used in an amount of equivalent or more to prepare an intermediate which is then reduced to obtain the objective compound, but these processes are not economical since the reaction process is long or cost and labor are required for recovering by-products. Further the process (iv) also has drawbacks that the reducing agent is not only expensive, but also difficult to deal with, still further, in the case of the processes and (v) wherein high pressure catalytic reduction is carried out in an autoclave with Raney nickel catalyst it is necessary to employ an expensive apparatus in order to raise the yield. Particularly the process (iii) has an additional disadvantage that the reaction process is prolonged since it is carried out via an aldoxime as an intermediate, and further hydroxylamine used in the preparation of this aldoxime is also relatively expensive.

SUMMARY OF THE INVENTION

The object of the present invention is to provide a process for producing aminobenzylamine directly from nitrobenzaldehyde as starting material, not via nitrobenzaldoxime, and with a high yield.

The present invention resides in a process for producing m-or p-aminobenzylamine which comprises subjecting a nitrobenzaldehyde expressed by the formula:

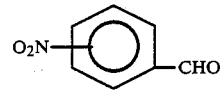

wherein nitro group is located at m-position or p-position, and ammonia to catalytic reduction in the presence of a reducing catalyst in an organic solvent.

DETAILED DESCRIPTION OF THE INVENTION

In the catalytic reduction of the present invention, reduction may be carried out in the presence of ammonia in an amount of one mol or more, preferably 7 to 15 mols based on one mol of nitrobenzaldehyde. Ammonia in a gaseous form may be used, but the use of liquid ammonia is preferable in the present invention.

As for the organic solvent used, aliphatic lower alcohols having a high solubility of ammonia therein such as methanol, ethanol, etc., are preferably used and advantageous. The amount of the solvent used has no particular limitation, but 1 to 15 times by weight the amount of raw material is usually sufficient.

Examples of the reducing catalyst used in the present invention are those of noble metals such as platinum, palladium, rhodium, etc., and Raney catalysts. When noble metal catalysts are used they may be used even in the form of metal, but usually catalysts having noble metals supported on the surface of a carrier such as carbon, silica gel, alumina, etc., are used. Particularly, Raney nickel, Raney cobalt, etc., are commercially advantageous. The amount of the catalysts used is in the range of 0.01 to 30% by weight in terms of metal based on raw material nitrobenzaldehyde. Usually a range of 2 to 20% by weight is preferred in the case where Raney catalysts are used, while a range of 0.1 to 5% by weight, in the case where noble metals supported on a carrier are used.

Further, the reaction temperature is preferably in the range of 30° to 150° C., particularly 60° to 120° C.

As for the reaction pressure employed, higher ones are 1 better, but usually a range of 10 to 150 kg/cm² G is suitable. If the reaction pressure is so low that the reaction does not proceed rapidly, there is a tendency of reduction in the yield.

In a general embodiment of the process of the present invention, a catalyst may be added to the raw material in a state where it is dissolved or suspended in a solvent, followed by introducing ammonia and successively introducing hydrogen to carry out the reaction until its absorption ceases. In a preferred embodiment, the raw material and ammonia (liquid ammonia) are dissolved in a solvent, and while the resulting mixed solution is introduced in divided manner into a reactor having hydrogen, a solvent and a catalyst bed therein in advance, catalytic reduction is carried out at a desired pressure and temperature. At that time, the amount fed per addition of the mixed solution into the reactor varies somewhat depending on reaction conditions, but usually the amount is preferred to be adjusted so that the hydrogen absorption may cease within about 30 minutes after each addition of the aforementioned mixed solution of raw material, ammonia and solvent.

In the above process of introducing the mixed solution in divided manner, if the reaction pressure is low, it is necessary to reduce its divided amount introduced. This is uneconomical since the reaction time is prolonged as much.

In the process of the present invention, when the mixed solution is introduced in divided manner, the product is obtained with a higher yield than that in the case where it is introduced all at once, and also deterioration of the catalyst is small. Hence such a process is very advantageous even in view of its reuse. Further, the quantity of heat generated at the time of the reaction is easily controlled. After completion of the reaction, the catalyst is filtered off and the filtrate is distilled in a conventional manner to obtain the objective product.

The present invention will be described in more detail by way of Examples:

EXAMPLE 1

Into a 1 l capacity stainless autoclave were fed methanol (100 ml) and Raney nickel (made by Toyo CCI) (4.6 g in terms of nickel), followed by purging with nitrogen, successively purging with hydrogen to make the hydrogen pressure 40 kg/cm$^2$ G and raising the temperature up to 90° C.

Into a raw material vessel were fed p-nitrobenzaldehyde (60.4 g, 0.4 mol), methanol (400 ml) and liquid ammonia (ca. 80 g), which were then agitated at 0° to 5° C. for about 30 minutes to prepare a mixed solution. This solution was divided into 8 portions (each about 58 g), and introduced into the autoclave while the reaction temperature was kept at 90° C. Hydrogenation reaction for each portion of about 58 g fed into the autoclave required 5 to 15 minutes, and the total reaction time required was 80 minutes, during which 33 Nl in total of hydrogen was absorbed. After aging for 30 minutes, the reaction solution was allowed to cool down to room temperature, followed by taking out the reaction mass, filtering and subjecting the filtrate to vacuum distillation under a pressure of 5–6 mm Hg to obtain a fraction (distillation temperature: 129.5° C.–130° C.) (47.8 g, yield 97.7%). This fraction was found to have a purity of 99.9% according to gas chromatography, and it was confirmed to be p-aminobenzylamine. Further the values of elemental analysis were as follows:

| Elemental analysis (C$_7$H$_{10}$N$_2$) | C | H | N |
| --- | --- | --- | --- |
| Calculated value (%) | 68.8 | 8.25 | 22.9 |
| Observed value (%) | 68.8 | 8.29 | 22.8 |

EXAMPLE 2

Reaction was carried out in the same manner as in Example 1 except that p-nitrobenzaldehyde was replaced by m-nitrobenzaldehyde Reaction was complete in 115 minutes, during which hydrogen (32 Nl) was absorbed. Post-treatment as in Example 1 was successively carried out to obtain M-aminobenzylamine having a purity of 99.91% (46.7 g, yield 95.5%, b.p. 131°–132° C./6 mm Hg).

EXAMPLE 3

Into a 500 ml capacity stainless autoclave were fed p-nitrobenzaldehyde (30.2 g, 0.2 mol), methanol (200 ml) and Raney nickel (made by Toyo CCI) (4.6 g in terms of nickel), followed by purging with nitrogen gas, stirring for a while, introducing ammonia (about 40 g) while cooling the autoclave with ice water, successively pressurizing hydrogen to make the gauge pressure 40 Kg/cm$^2$ G, thereafter raising the temperature up to 70° C., and carrying out the reaction at this temperature for 60 minutes. As a result, hydrogen (16.3 Nl) was absorbed and the reaction was complete. The reaction solution was allowed to cool down to room temperature, followed by taking out the reaction mass, filtering and subjecting the filtrate to vacuum distillation under a pressure of 6 mm Hg to obtain a fraction (distillation temperature: 129.5°–130° C.) (22.0 g, yield 90.0%), corresponding to p-aminobenzylamine. Its purity according to gas chromatography was 99.91%.

EXAMPLE 4

Reaction was carried out as in Example 3 except that p-nitrobenzaldehyde was replaced by m-nitrobenzaldehyde. Reaction was complete in 55 minutes, during which hydrogen (15.8 Nl) was absorbed. Successively, post-treatment as in Example 3 was carried out to obtain m-aminobenzylamine having a purity of 99.94% (2.5 g, yield 88.0%, b.p. 131°–132° C./6 mm Hg).

EXAMPLE 5

The procedure of Example 1 was repeated except using 102 g (15 times by mol) of liquid ammonia.
Yield: 47.9 g, 97.9%.

EXAMPLE 6

The procedure of Example 1 was repeated except using 48 g (7 times by mol) of liquid ammonia.
Yield: 47.5 g, 97.1%.

EXAMPLE 7

The procedure of Example 1 was repeated except using methanol in a first addition of 100 ml and a second addition of 300 ml instead of 100 ml in the first addition and 400 ml in the second.
Yield: 47.5 g, 97.1%.

EXAMPLE 8

The procedure of Example 1 was repeated except using methanol in a first addition of 100 ml and a second addition of 300 ml instead of 100 ml in the first addition and 500 ml in the second.
Yield: 48.0 g, 98.1%.

EXAMPLE 9

The procedure of Example 1 wa repeated except using methanol in a first addition of 100 ml and a second addition of 300 ml instead of 100 ml in the first addition and 400 ml in the second and 9.2 g of Raney nickel instead of 4.6 g of Raney nickel.

Yield: 47.9 g, 97.9%.

EXAMPLE 10

The procedure of Example 1 was repeated except using methanol of 100 ml in the first and 300 ml in the second, 9.2 g of Raney nickel and temperature of 70° C. instead of temperature of 90° C.

Yields: 47.6 g, 97.3%.

EXAMPLE 11

The procedure of Example 10 was repeated except using m-nitrobenzaldehyde instead of p-nitrobenzaldehyde.

Yield: 95.3%.

EXAMPLE 12

The procedure of Example 1 was repeated except using 27 g (4 times by mol) of liquid ammonia.

Yield: 44.1 g, 90.2%.

EXAMPLE 13

The procedure of Example 3 was repeated except using 2.3 g of Raney nickel and temperature of 90° C. instead of 70° C.

Yield: 43.3 g, 88.5%.

Examples 12 and 13 and Examples 3 and 4 are presented for comparative tests.

What is claimed is:

1. A process for producing m- or p-aminobenzylamine which comprises subjecting nitrobenzaldehyde expressed by a formula,

wherein nitro group is located at m-position or p-position, and ammonia to catalytic reduction in the presence of a reducing catalyst in an aliphatic lower alcohol, in said catalytic reduction nitrobenzaldehyde and liquid ammonia in an amount of 7 to 15 times by mol that of nitrobenzaldehyde are in advance made a mixed solution which is then introduced in divided manner, said catalytic reduction is carried out at a temperature in the range of 60° to 120° C.

2. A process according to claim 1 wherein said reducing catalyst is Raney nickel or Raney cobalt.

* * * * *

UNITED STATES PATENT AND TRADEMARK OFFICE
CERTIFICATE OF CORRECTION

PATENT NO. :     4,978,792
DATED      :     Dec. 18, 1990
INVENTOR(S) :    Nagata et al.

It is certified that error appears in the above-identified patent and that said Letters Patent is hereby corrected as shown below:

On the title page, below item [22] after the filing date, please insert the following:

--Foreign Application Priority Data

Nov. 16, 1983 [JP]   Japan        214038/1983
Jan. 9, 1984 [JP]    Japan        821/1984--

Signed and Sealed this

Seventeenth Day of November, 1992

Attest:

DOUGLAS B. COMER

*Attesting Officer*     *Acting Commissioner of Patents and Trademarks*

UNITED STATES PATENT AND TRADEMARK OFFICE
CERTIFICATE OF CORRECTION

PATENT NO. : 4,978,792
DATED : Dec. 18, 1990
INVENTOR(S) : Nagata et al.

It is certified that error appears in the above-identified patent and that said Letters Patent is hereby corrected as shown below:

Column 1, line 68, after "processes" insert --(iii)--.
　　　Column 2, line 61, delete "1".
　　　Column 4, line 38, delete "2.5g" and substitute therefor --21.5g--.
　　　Column 4, line 66, delete "wa" and substitute therefor --was--.

Signed and Sealed this

Fifth Day of January, 1993

Attest:

DOUGLAS B. COMER

Attesting Officer　　　Acting Commissioner of Patents and Trademarks